(12) United States Patent
Li et al.

(10) Patent No.: US 6,913,765 B2
(45) Date of Patent: Jul. 5, 2005

(54) CONTROLLING RESORPTION OF BIORESORBABLE MEDICAL IMPLANT MATERIAL

(75) Inventors: Jianmin Li, Lexington, MA (US); Samuel Baldwin, Newton, MA (US); Tim Harrah, Newton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/813,780

(22) Filed: Mar. 21, 2001

(65) Prior Publication Data

US 2002/0138154 A1 Sep. 26, 2002

(51) Int. Cl.$^7$ .................................................. A61F 2/02
(52) U.S. Cl. .................. 424/426; 604/890.1; 604/891.1
(58) Field of Search ............................... 424/426, 423, 424/422, 427, 428, 430, 433; 514/772.3; 604/890.1, 891.1

(56) References Cited

U.S. PATENT DOCUMENTS

| | | |
|---|---|---|
| 2,485,512 A | 10/1949 | Rose |
| 2,541,804 A | 2/1951 | Wormell |
| 2,689,809 A | 9/1954 | Fessler |
| 2,712,672 A | 7/1955 | Calcagno |
| 2,791,518 A | 5/1957 | Stokes, Jr. et al. |
| 2,847,713 A | 8/1958 | Weingand |
| 2,897,547 A | 8/1959 | Weingand |
| 3,271,496 A | 9/1966 | Michaels |
| 3,975,350 A | 8/1976 | Hudgin et al. |
| 4,137,921 A | 2/1979 | Okuzumi et al. |

(Continued)

FOREIGN PATENT DOCUMENTS

| | | |
|---|---|---|
| DE | 2827289 | 1/1979 |
| EP | 0065884 A1 | 12/1982 |
| EP | 2151244 A | 7/1985 |
| EP | 0213908 A2 | 3/1987 |
| EP | 0271216 A2 | 6/1988 |
| EP | 0341745 A1 | 11/1989 |
| EP | 0380254 A2 | 8/1990 |
| EP | 0454373 A2 | 10/1991 |
| EP | 04146218 | 5/1992 |
| EP | 0507604 A2 | 10/1992 |

(Continued)

OTHER PUBLICATIONS

Andrade, Joseph D., "Hydrogels for Medical and Related Applications", Aug. 27–28, 1975, p. 1–36 (Editor, presented article at that time); AM. Chem. Soc. 1976.

(Continued)

Primary Examiner—Carlos A. Azpuru
(74) Attorney, Agent, or Firm—Mayer Fortkort & Williams, PC; Keum J. Park, Esq.; David B. Bonham, Esq.

(57) ABSTRACT

The resorption of a medical implant can be controlled with the use of particles embedded in a resorbable bulk material forming the implant or portion thereof. The implant can be removed from a body of a mammal by natural biological mechanisms after use. The resorption of the implant can involve swelling and/or hydrolyzing of the particles within the implant upon contact with a body fluid such that porosity and flow of fluid within the bulk material of the implant is increased. Resorption of the implant may also involve the use of particles with magnetic properties embedded within the implant such that an applied magnetic field causes the particles to vibrate within the bulk material thereby increasing the porosity and thus the flow of fluid, hence facilitating resorption of the implant. The resorption rate of the implant can be controlled by modulating swelling, hydrolysis, or movement of the embedded particles.

35 Claims, 6 Drawing Sheets

U.S. PATENT DOCUMENTS

| | | | |
|---|---|---|---|
| 4,265,927 A | 5/1981 | Ericksson et al. |
| 4,286,341 A | 9/1981 | Greer et al. |
| 4,339,295 A | 7/1982 | Boretos et al. |
| 4,366,183 A | 12/1982 | Ghommidh et al. |
| 4,439,322 A | 3/1984 | Sonoda et al. |
| 4,527,293 A | 7/1985 | Eckstein et al. |
| 4,548,844 A | 10/1985 | Podell et al. |
| 4,582,865 A | 4/1986 | Balazs et al. |
| 4,592,920 A | 6/1986 | Murtfeldt |
| 4,605,691 A | 8/1986 | Balazs et al. |
| 4,613,517 A | 9/1986 | Williams et al. |
| 4,636,524 A | 1/1987 | Balazs et al. |
| 4,650,488 A | 3/1987 | Bays et al. |
| 4,716,154 A | 12/1987 | Malson et al. |
| 4,716,224 A | 12/1987 | Sakurai et al. |
| 4,801,475 A | 1/1989 | Halpern et al. |
| 4,814,120 A | 3/1989 | Huc et al. |
| 4,838,876 A | 6/1989 | Wong et al. |
| 4,851,521 A | 7/1989 | dellaValle et al. |
| 4,863,907 A | 9/1989 | Sakurai et al. |
| 4,878,907 A | 11/1989 | Okada et al. |
| 4,888,016 A | 12/1989 | Langerman |
| 4,902,295 A | 2/1990 | Walthall et al. |
| 4,906,237 A | 3/1990 | Johansson et al. |
| 4,923,645 A | 5/1990 | Tsang et al. |
| 4,941,870 A | 7/1990 | Okasa et al. |
| 4,948,575 A | 8/1990 | Cole et al. |
| 4,957,744 A | 9/1990 | dellaValle et al. |
| 4,965,353 A | 10/1990 | dellaValle et al. |
| 4,981,487 A | 1/1991 | da Costa |
| 4,997,443 A | 3/1991 | Walthall et al. |
| 5,049,138 A | 9/1991 | Chevalier et al. |
| 5,057,606 A | 10/1991 | Garbe |
| 5,061,738 A | 10/1991 | Solomon et al. |
| 5,077,352 A | 12/1991 | Elton |
| 5,085,629 A | 2/1992 | Goldbert et al. |
| 5,089,606 A | 2/1992 | Cole et al. |
| 5,522,895 A | 6/1996 | Mikos |
| 5,551,954 A | 9/1996 | Buscemi et al. |
| 5,741,329 A | 4/1998 | Agrawal et al. |
| 5,820,918 A | 10/1998 | Ronan et al. |
| 6,060,534 A | * 5/2000 | Ronan et al. ............... 523/113 |
| 6,110,484 A | * 8/2000 | Sierra ........................ 424/426 |

FOREIGN PATENT DOCUMENTS

| | | |
|---|---|---|
| EP | 0579004 A1 | 1/1994 |
| EP | 0645150 A1 | 3/1995 |
| JP | 06233855 | 8/1994 |
| WO | 89/05671 | 6/1989 |
| WO | 90/10020 | 9/1990 |
| WO | 91/07200 | 5/1991 |
| WO | 92/13579 | 8/1992 |
| WO | 92/18098 | 10/1992 |
| WO | 93/09176 | 5/1993 |
| WO | 9932536 | 7/1999 |
| WO | 01/32072 | 5/2001 |

OTHER PUBLICATIONS

K cvara et al., "Gel–Fabric Prostheses of the Ureter", *Journal of Biomedical Research,* vol. 1, pp. 325–336 (1967).

Ross, "Living Cure" (Science and the Citizen), *Scientific American,* Jun. 1993, pp. 18–23.

Kishida et al., Chemical and Pharmaceutical Bulletin, Pharmaceutical Society of Japan, Tokyo, JP, vol. 37, No. 7, 1989, pp. 1954–1956, XP002101838, ISSN: 0009-2363.

PCT International Search Report, PCT/US 02/07600.

Dagani, Ron, "Nanocomposite Extraordinaire—Magnetic Nanoparticles Freely Rotate Inside Nanocavities In A Solid Matrix", vol. 78, No. 23, p. 13, Chemical & Engineering News (Jun. 5, 2000).

Edelman, E.R., et al. "Regulation of Drug Release From Polymer Matrices By Oscillating Magnetic Fields", vol. 19, pp. 67–83, Journal of Biomedical Materials Research (1985).

* cited by examiner

CONTROLLING RESORPTION OF BIORESORBABLE MEDICAL IMPLANT MATERIAL

TECHNICAL FIELD

This invention generally relates to medical implants. More particularly, the invention relates to devices, methods, and compositions for use in medical implants that resorb in a body of a mammal.

BACKGROUND INFORMATION

Medical implants have a variety of applications including kidney drainage and vascular surgery. Examples of medical implants include a ureteral stent used for drainage of urine from the kidney to the bladder and a vascular graft used for maintaining blood flow. Medical implants generally have to be removed from the body by an invasive procedure. Medical implants that are left in vivo after use may cause complications such as inflammation and other foreign body responses.

SUMMARY OF THE INVENTION

In accordance with the invention, a medical implant is removed from a patient's body by non-invasive means, such as by resorption of the medical implant by natural biological mechanisms. Non-invasive removal of a medical implant avoids pain and suffering often associated with invasive and surgical procedures. In addition, a non-invasive removal procedure reduces medical expenses and lost productivity of the patient.

The present invention relates to compositions, devices, and methods that are useful in controlled in vivo resorption of bioresorbable medical implants. as by resorption of the implant material followed by normal elimination in a body fluid such as urine or feces. By using natural biological mechanisms of elimination, patient discomfort and the risk of complications to the patient is minimized compared to invasive procedures, such as surgical or endoscope procedures. Another objective of this invention is to provide procedures in which removal of an implant is non-invasive, controllable, and predictable. In one embodiment, the rate of removal of the implant is pre-selectable. Medical implants according to the invention can take various shapes and can include stents, catheters, cannulas, plugs, fillers, constrictors, sheets, bone anchors, plates, rods, seeds, and tubes, for example.

In one aspect, the invention generally features a composition for use in a medical device in a mammal (such as a human or an animal) that includes a bioresorbable bulk material and particles embedded therein. The particles cause the bioresorbable bulk material to resorb at a controllable rate upon contact with a body fluid. The compositions, medical devices, and methods of the invention generally are suitable for use in any mammal including a human or animal. In one embodiment, the medical device includes a bioresorbable bulk material with embedded resorbable particles causing the bioresorbable bulk material to resorb at a controllable resorption rate upon contact with a body fluid. The embedded particles have a different and faster resorption rate than the bioresorbable bulk material and cause the bioresorbable bulk material to resorb upon contact with a body fluid. In another embodiment, the medical device includes a bioresorbable bulk material with embedded particles having magnetic properties.

The composition of the invention may include a bulk bioresorbable material of ionically crosslinked polymeric materials, e.g., an ionically crosslinked polymer hydrogel and having a water content of less than 90% by weight and possesses sufficient mechanical strength to serve as any of the medical implants mentioned above. Each of the resorbable particles may include, for example, an organic compound, a soluble or degradable inorganic compound, a sugar or water-soluble organic salt, an organic or inorganic crystal powder aggregate, or a water-swellable polymer.

In another aspect, the invention generally features a method for controlling resorption of a bioresorbable material in a medical device for use in a mammal. In one embodiment, the method includes the steps of providing a bioresorbable bulk material, embedding resorbable particles in the bioresorbable bulk material, and contacting a body fluid with the medical device thereby causing the bioresorbable bulk material to resorb at a controllable resorption rate. The particles can have a different and faster resorption rate than that of the bioresorbable bulk material.

In another embodiment, a method for controlling resorption of a bioresorbable material in a medical device includes providing a bioresorbable bulk material, embedding in the bioresorbable bulk material particles having a pre-selected magnetic property, exposing the medical device to a magnetic field, and inducing activation and/or vibration of the particles thereby causing the bioresorbable bulk material to resorb at a controllable resorption rate.

In yet another embodiment, a method for controlling resorption of a bioresorbable material in a medical device includes providing a bioresorbable bulk material shaped as a medical device, providing a coating material including a dissolvable polymeric material that allows for diffusion of a body fluid through the coating material at a pre-selected rate, and coating the medical device with the coating material.

In yet another aspect, the invention generally features a system for controlled delivery in the body of a mammal of a pharmaceutical agent. The system includes a carrier device having coated thereon a bioresorbable, ionically or covalently crosslinked polymeric material and incorporated therein a pharmaceutical agent.

In yet another aspect, the invention generally features a coating material for use in a medical device for regulating resorption of the medical device. The coating material includes a bioresorbable ionically or covalently crosslinked polymeric material that allows diffusion into the medical device by a body fluid at a controllable rate.

These and other features, aspects, and advantages will become more apparent from the following description, drawings, and claims.

BRIEF DESCRIPTION OF THE DRAWINGS

The drawings are not necessarily to scale, emphasis instead generally being placed upon illustrating the principles of the invention.

DESCRIPTION

The resorption rate of a bioresorbable material used in medical implants may be controlled by effectively controlling the degree of porosity and thus the diffusion rate of a fluid in the implant material. The porosity of the implant material may be created or controlled by embedding in a bulk material resorbable particles that resorb at a different and faster rate than the bulk material. In general, the bioresorbable materials forming the bulk component of the medical device are permeable to certain body fluids including water and small ionizable molecules dissolved therein. A body fluid is capable of penetrating the matrix of the bulk material through various mechanisms (e.g., diffusion, migration, or capillary action) to reach the embedded particles. The fluid causes the resorbable particles to resorb once in contact with the particles. The resorption of the particles leads to the formation of voids in the matrix of the bulk material. These voids contribute to an increase in porosity of the bulk material, leading to a greater fluid flow in the matrix of the bulk material thereby speeding up its bioresorption.

When the implant is broken into smaller fragments, the resorption process becomes more effective and poses less health risks. The existence of large fragments of the implant could clog the flow of the body fluid such as blood potentially causing serious complications. Therefore, by embedding resorbable particles that swell or move inside the bulk implant material, the implant frame and large fragments of the implant may be broken down into much smaller fragments. In addition, fragmentation increases the contact area with the body fluid thereby facilitating resorption of the implant materials remaining in the fragments.

The porosity of the bulk material may also be increased by agitation of the particles within the matrix of the bulk material thereby structurally modifying or rupturing the matrix thereby creating voids around them. These voids are then available for the fluid flow as described above. Accordingly, the present invention features resorbable medical devices, and methods and compositions for achieving their controlled resorption.

Compositions and Medical Devices

In one aspect, the invention is directed to compositions useful in the manufacture of medical devices for use in a mammal. The compositions include a bulk material that is bioresorbable and has resorbable particles embedded therein. In another embodiment, the compositions may include a bioresorbable bulk material that has magnetic particles embedded therein.

The bioresorbable bulk material may be a reversibly ionically crosslinked polymeric material, which can include an ionically crosslinkable polymer and crosslinking ions. The ionically crosslinkable polymeric material may be anionic or cationic and may include, but is not limited to, at least one polymer or copolymer such as polyacrylic acids, polymethacrylic acid, polyethylene amine, polysaccharides, alginic acid, pectinic acids, carboxy methyl cellulose, hyaluronic acid, heparin, chitosan, carboxymethyl chitosan, carboxymethyl starch, carboxymethyl dextran, heparin sulfate, chondroitin sulfate, cationic starch, and salts thereof. Illustrative examples of cationic crosslinking ions include polycations such as calcium, magnesium, barium, strontium, boron, beryllium, aluminium, iron, copper, cobalt, lead, and silver ions. Illustrative examples of anionic crosslinking ions include polyanions such as phosphate, citrate, borate, succinate, maleate, adipate and oxalate ions, and, more broadly, anions derived from polybasic organic or inorganic acids. In one embodiment, the crosslinking cations are barium, and the crosslinking anions are phosphates. The bioresorbable bulk material may also be a reversibly, covalently crosslinked, polymeric material.

The bulk material may be a hydrogel having a water content of less than 90% by weight and possessing sufficient mechanical strength to serve as, for example, a stent, a catheter, a cannula, a plug, a constrictor, a sheet, a filler, a bone anchor, a plate, a rod, a seed, a tube, or a portion thereof. As used herein, the term "hydrogel" indicates a material that is water permeable, yet water insoluble in its crosslinked form, but would release water-soluble components upon removal of the crosslinks. A device may be in its hydrogel form or in a dehydrated form.

As used herein, a soluble material is a material that has a water solubility such that upon exposure to a body fluid an amount of the material will dissolve or erode over time. "Body fluid" here refers to fluids in the body of a mammal including, but not limited to, blood, urine, saliva, lymph, plasma, gastric, biliary, or intestinal fluids, seminal fluids, and mucosal fluids or humors. A degradable material is a material that can decompose, degenerate, degrade, depolymerize, or otherwise reduce the molecular weight of the starting compound(s) such that the resulting compound (s) is soluble in water or, if insoluble, can be suspended in a body fluid and transported away from the implantation site without clogging the flow of the body fluid. A resorbable material is a material that is soluble, degradable as defined above, or is an aggregate of soluble and/or degradable material(s) with insoluble material(s) such that, with the resorption of the soluble and/or degradable materials, the residual insoluble materials are of sufficiently fine size such that they can be suspended in a body fluid and transported away from the implantation site without clogging the flow of the body fluid. Ultimately, the particles are eliminated from the body either by excretion in perspiration, urine or feces, or dissolved, degraded, corroded or otherwise metabolized into soluble components that are then excreted from the body. A bioresorbable material is a resorbable material that is biocompatible. A biocompatible material is a material that is compatible with living tissue or a living system, non-toxic or non-injurious and do not cause immunological reaction or rejection.

Generally, the particles embedded in the bioresorbable bulk material facilitate the resorption of the bioresorbable bulk material at a controllable resorption rate upon contact with a body fluid. The bioresorbable bulk material resorbs at a different and faster rate than when it would if there were no particles embedded in the bulk material. The resorption rate of the bioresorbable material can be controlled by varying the chemical and physical properties of the particles, their size, shape, amount, and distribution, etc. The particles may be resorbable or have magnetic properties. The resorbable particles generally resorb at a different and faster rate than the bioresorbable bulk material. The resorbable particles may include a swelling agent, an hydrolysable agent, or a soluble agent or a combination thereof. These agents may be organic compounds, polymeric compounds, soluble or degradable inorganic compounds, and/or organic or inorganic crystals or powder aggregates. The particles may also include a polymeric material, e.g., polysaccharides, polyglycolic acid, polylactic acid, cellulose derivatives, hyaluronic acid, polylactams, hydrogels or other colloid. As an illustrative example, the resorbable particles may include aggregates of metal oxides and a water-soluble component such as a gum, a sugar, or a salt. In these aggregates, the metal oxide may have magnetic properties. The magnetic particles may also include a magnetic material coated with a protective coating to prevent degradation of the magnetic material by a body fluid and loss of magnetic properties.

In another aspect, the invention is directed to medical devices made of these compositions. Such medical devices include stents, catheters, cannulas, plugs, fillers, constrictors, sheets, bone anchors, plates, rods, seeds, tubes, or portions thereof. Exemplary medical devices according to the invention are shown in FIGS. 1a–i. Devices according to the invention may take many shapes or configurations other than those depicted in FIGS. 1a–i, as these are only examples and are not intended to encompass all the embodiments of the invention. Depending on the application, the entire device or one or more portions of the device may be made of the bioresorbable compositions of the present invention.

Figure 1A:
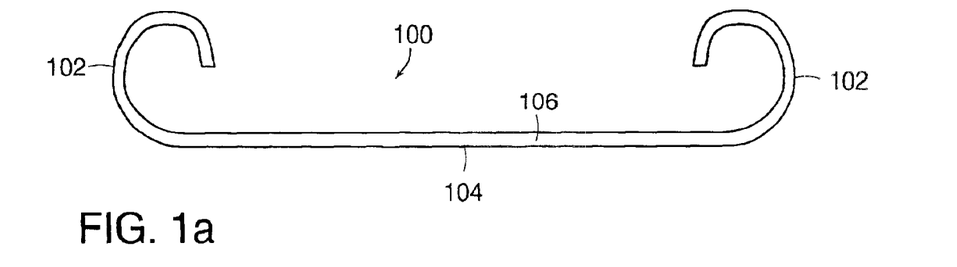
FIGS. 1a–1i show some exemplary embodiments of medical devices according to the invention which include a stent (FIG. 1a), a seed (FIG. 1b), a cannula (FIG. 1c), a bone anchor (FIG. 1d), a sheet (FIG. 1e), a plate (FIG. 1f), a rod (FIG. 1g), a plug (FIG. 1h), and a constrictor (FIG. 1i).

FIG. 1a depicts a tubular stent 100 that includes two coil-shaped end portions 102, a central portion 104, a lumen or passageway 106 within the tube from one end to the other. Stents may be used for maintaining the patency of a body vessel such as, for example, urinary drainage from the kidney to the bladder in patients with ureteral obstruction or injury, or to protect the integrity of the ureter in a variety of surgical manipulations. The device may be extruded or molded with the bioresorbable composition of this invention such that the entire device is made thereof or such that only one or more portions of the device include the compositions of the invention, such as one or both end portions 102, for example.

Figure 1B:
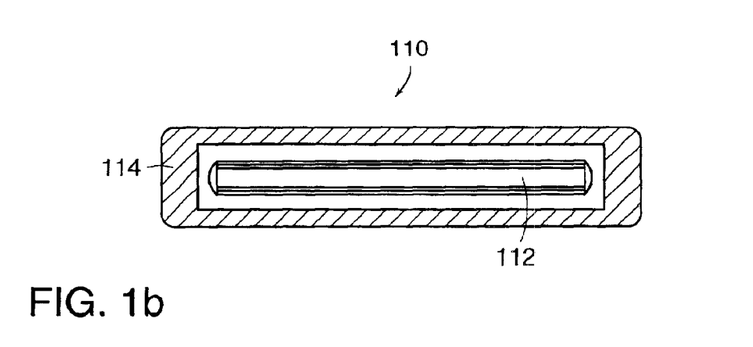

FIG. 1b depicts a seed 110 shaped into an elongated pellet that includes an active substrate 112 (such as a medicine) within a shell or coating 114 made of the resorbable composition according to the invention. Alternatively, the medicine may be mixed throughout the seed, and the shape of the seed may be accommodated for the intended use into other shapes, such as spherical, egg-shape, for example. Such seeds may be used for delivering medicine to a specific organ such as in prostate hyperplasia and to provide control release of the medicine into the organ upon resorption of the seed. See also, U.S. Pat. No. 4,697,575 (incorporated herein by reference in its entirety). The entire device may be made of the bioresorbable material of the invention as the bulk material with the medicine embedded therein that is introduced during manufacture. Alternatively, only the shell or coating 114 may be made of the bioresorbable material.

Figure 1C:
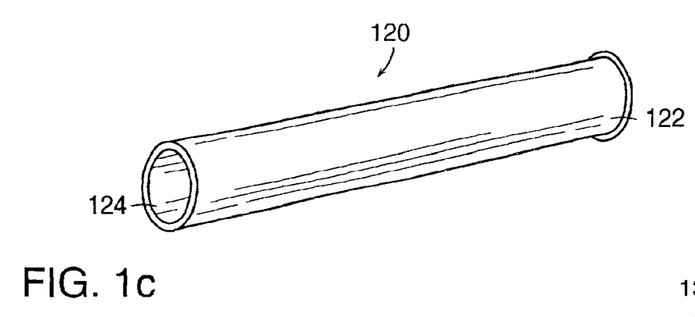

FIG. 1c depicts a cannula 120 that includes a tube 122 and a lumen or passageway 124. Cannulas are generally used to gain access to an organ or vessel in a body percutaneously or through a natural body opening. Similarly to a cannula, a catheter is an elongated tube for insertion percutaneously or through a natural body opening into a body cavity, duct, or vessel to allow the passage of a fluid or distend a passageway. Catheters are generally used for the drainage of urine from the bladder through the urethra, for insertion into a blood vessel for diagnostic purposes, or to drain an abscessed area. A cannula or catheter may be extruded or molded with the bioresorbable composition of this invention such that the entire device is made thereof or such that only one or more portions of the device include the compositions of the invention, such as one or both end portions 122 or a middle section therebetween for example.

Figure 1D:
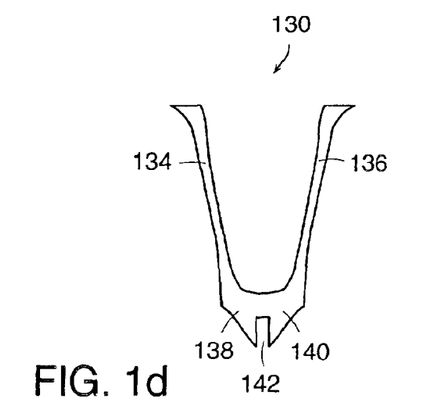

FIG. 1d depicts a bone anchor 130 that includes anchoring legs 134, 136 which include distal portions 138, 140, respectively, in the form of tapered cones separated by a slot 142. See U.S. Pat. No. 6,146,406 (incorporated herein by reference in its entirety). Bone anchors are commonly used to attach soft tissue to bone, e.g., during rotator cuff ligament reconstruction. An anchor having an attached suture can be placed into a bone hole. The suture can then be used to attach soft tissue to the bone. It is beneficial to have the entire bone anchor or one or more portions, e.g., a portion of or the entire of one or both legs 134 and 136, made of the resorbable composition of the invention. After secure attachment of the soft tissue and the suture, the implanted bone anchor will then resorb over time without the need for surgical removal.

Figure 1E:
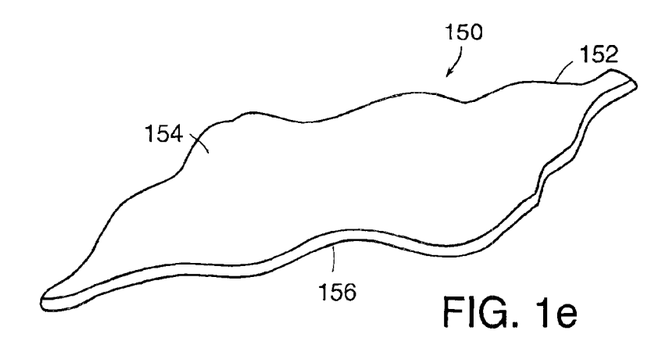

FIG. 1e depicts a sheet 150 that includes a flexible and flat member 152, a top surface 154 and bottom surface 156. For example, a sheet may be used as anti-adhesion barrier to isolate tissues or organs such that they do not adhere to the organ or tissue. A sheet may be made with the bioresorbable composition of this invention such that the entire sheet is made thereof or such that only one or more portions of the sheet include the compositions of the invention, e.g., one or both surfaces 154 and 156.

Figure 1F:
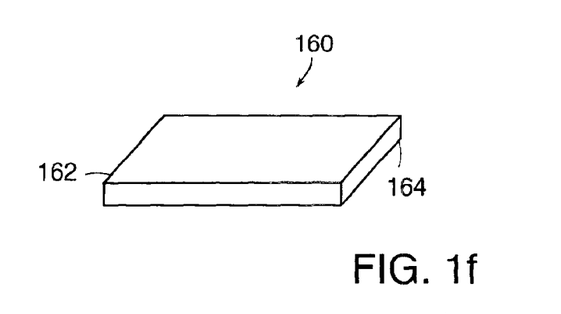

Similarly, as depicted in FIG. 1f, a plate 160 includes a flat member 162 that is typically rigid. For example, a plate may be used as an organ support or as a space filler. A plate may be made with the bioresorbable composition of this invention such that the entire plate is made thereof or such that only one or more portions of the plate include the compositions of the invention, e.g., one or all corners 164.

Figure 1G:
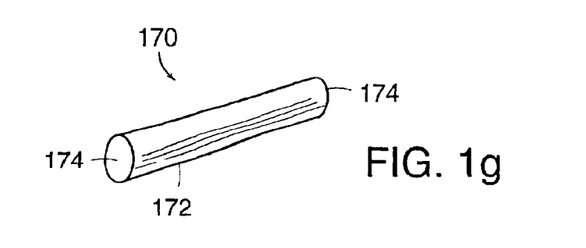

As depicted in FIG. 1g, a rod 170 includes an enlongated member 172 and end portions 174. A rod may be made with the bioresorbable composition of this invention such that the entire rod is made thereof or such that only one or more portions of the rod include the compositions of the invention, e.g., one or both end portions 174 or a portion therebetween. For example, a plate may be used as an organ support or as a space filler.

Figure 1H:
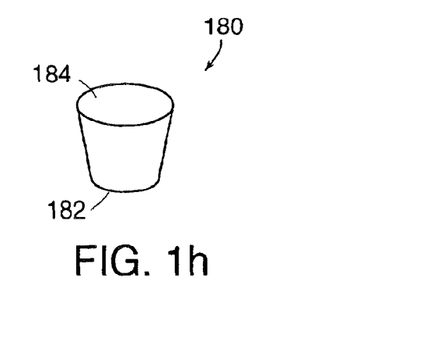

FIG. 1h depicts a plug 180 having a proximal end portion 182 and a distal end portion 184 that is usually used to stop fluid flow. A plug may or may not be formed in situ. A plug may be made with the bioresorbable composition of this invention such that the entire plug is made thereof or such that only one or more portions of the plug include the compositions of the invention, e.g., one or both end portions 182 and 184.

Figure 1I:
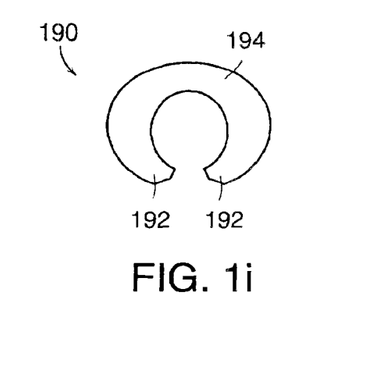

FIG. 1i depicts a constrictor 190 that includes arms 192 and a body portion 194. A constrictor may be used to control the location of a body part or to prevent aneurysms. A constrictor may be made with the bioresorbable composition of this invention such that the entire constrictor is made thereof or such that only one or more portions of the constrictor include the compositions of the invention, e.g., one or both arm portions 192.

A medical device according to the invention can also be a filler, i.e., one or more compositions that take the shape of a body cavity or bulk up the tissue surrounding a body cavity. For example, a filler may be used to fill up an aneurysm or assist in establishing control over the passage of a body fluid such as in gastric or ureteral reflux, or urinary incontinence. In these applications, the bioresorbable composition of the invention is injected in the body cavity to be filled and bulked in the form of a gel or liquid and allowed to solidify by exposure to crosslinking mechanisms such as ionic or covalent crosslinking mechanisms.

Figure 2:
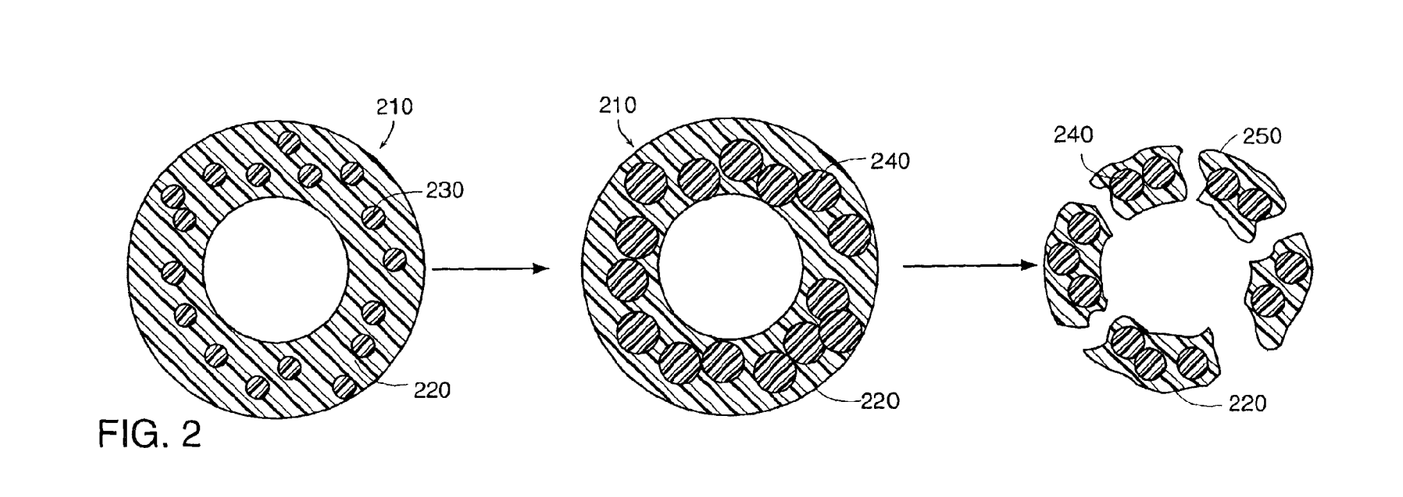
FIG. 2 is a cross-sectional schematic view of an embodiment of a medical device according to the invention, illustrating the control of resorption by swelling of embedded particles within the implant material.

Referring to FIG. 2, which is a cross-sectional view of a tubular medical device 210 such as a stent, the device 210 is fabricated from a bulk bioresorbable material 220 with embedded resorbable particles 230. The resorbable particles 230, each of which has an agent that swells upon contact with a body fluid, can be incorporated into the bioresorbable bulk material 220 during the manufacture of the device 210, for example, by co-extrusion or molding. The inclusion of resorbable particles 230 in the bioresorbable bulk material 220 and the resulting swelled particles 240 cause the medical implant to break up into small fragments 250. The fragmentation process prevents large implant frame or fragments from clogging the flow of body fluids. It also increases the contact area of the bioresorbable bulk material of the implant 210 with the body fluid. As a consequence, the diffusion rate of the fluid in the matrix increases, promoting resorption and mechanical degradation of the matrix structure of the medical implant. The swelling is especially effective when the ionic linkages are partially removed as well as when outward diffusion of crosslinking ions have weakened the mechanical strength of the remaining implant frame.

Figure 3:
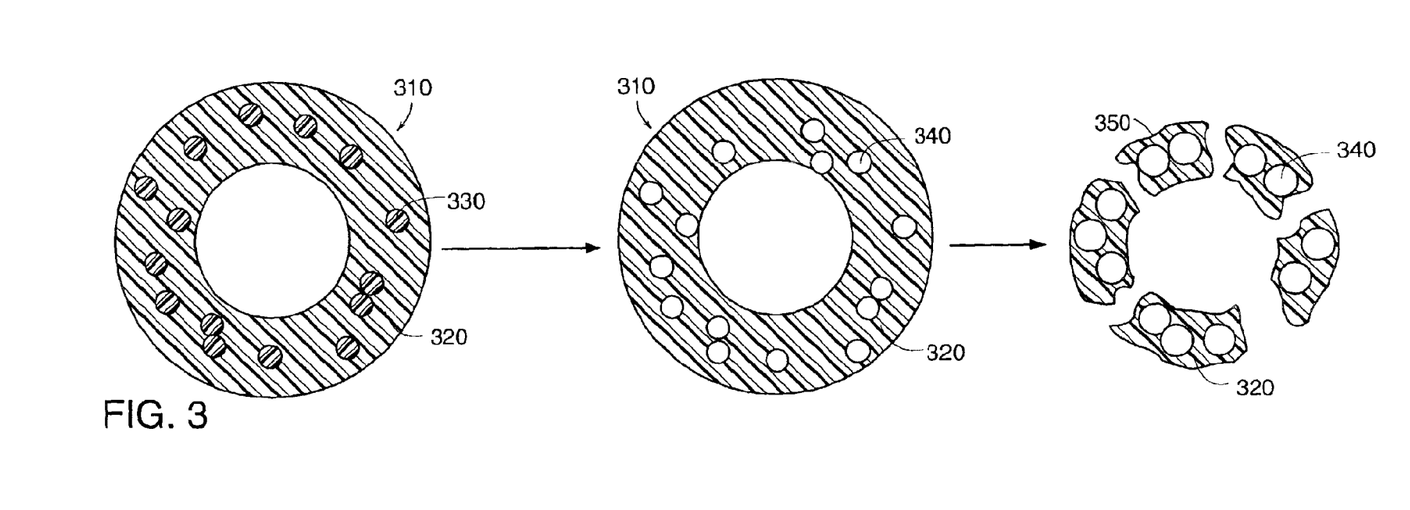
FIG. 3 is a cross-sectional schematic view of an embodiment of a medical device according to the invention, illustrating the control of resorption by hydrolysis of embedded particles within the implant material.

Referring to FIG. 3, which is a cross-section view, a medical device 310, such as a stent, is fabricated from a bulk bioresorbable material 320 having therein embedded resorbable particles 330. Resorbable particles 330, each of which has an agent that hydrolyzes upon contact with a body fluid, can also be incorporated into the bioresorbable bulk material 320 during the manufacture of the medical device 310, for example, by co-extrusion or molding. The agent hydrolyzes within the matrix upon contact with the body fluid. The embedded particles 330 resorb by hydrolysis upon contact with the body fluid producing water-soluble by-products. Hydrolysis of the particles produces voids 340 and increases the porosity of the matrix of the bioresorbable bulk material 320, resulting in an increased diffusion rate that promotes resorption and degradation of the bioresorbable bulk material 320. The device as a result breaks into smaller fragments 350. The particles may include a hydrolyzable polymer such as polysaccharides, polyglycolic acid, polylactic acid, polycaprolactone, or copolymers of any two or three of glycolic acid, lactic acid, and caprolactone monomers.

Figure 4:
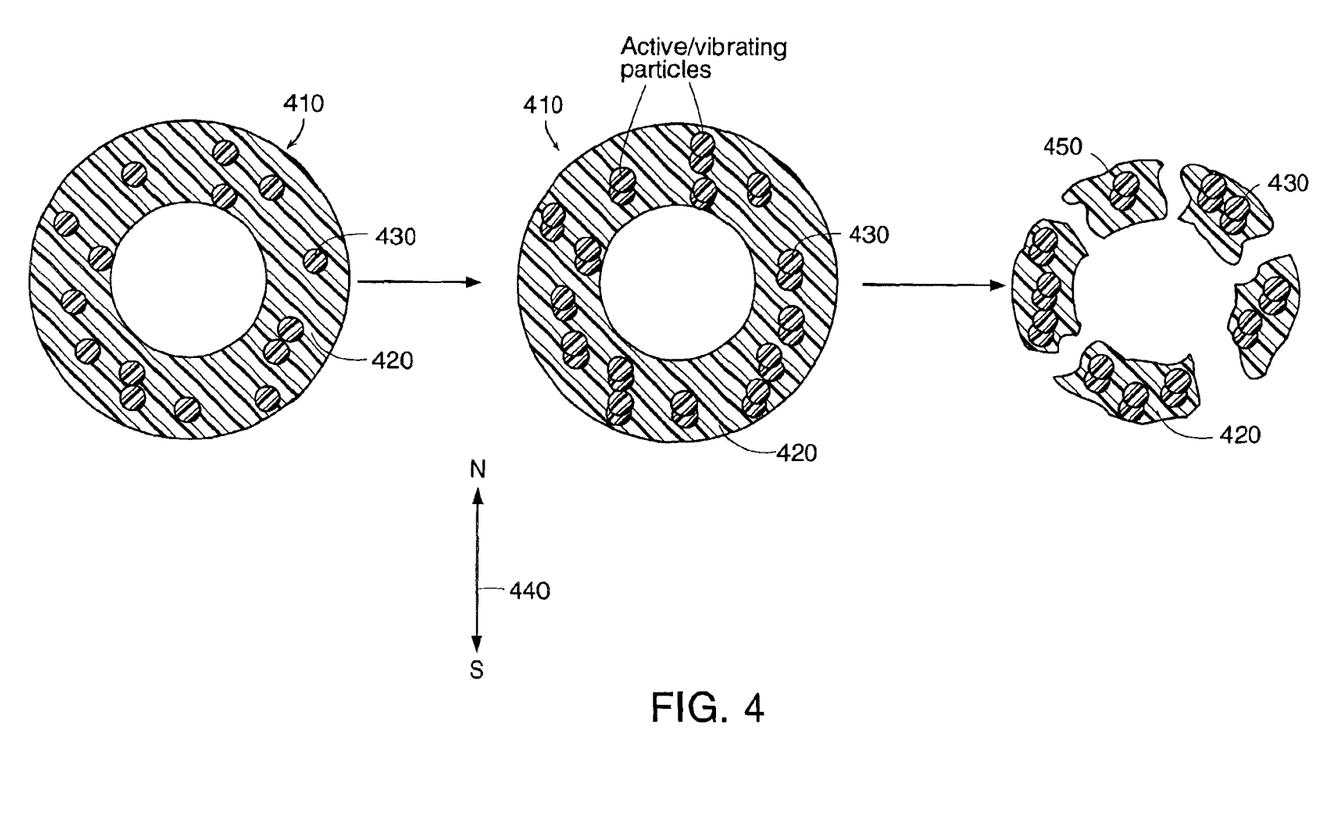
FIG. 4 is a cross-sectional schematic view of an embodiment of a medical device according to the invention, illustrating the control of resorption by magnetic activation of embedded particles within the implant material.

Referring to FIG. 4, which is a cross-sectional view, a medical device 410, such as a stent, is fabricated from a bulk resorbable material 420 having therein embedded particles 430. Each of the particles 430 may include one or more materials with magnetic, paramagnetic, and/or superparamagnetic (generally referred to hereinafter as simply "magnetic") properties. The particles 430 having magnetic properties may be embedded into the bioresorbable bulk material 420 during the manufacture of a medical device 410, for example, by co-extrusion or molding. The embedded particles 430 can be transiently or continuously stimulated by the use of a magnetic field, such as an oscillating magnetic field 440. The embedded particles 430 respond to the magnetic field by moving and/or vibrating within the matrix of the bioresorbable bulk material thereby causing fragmentation of the implant frame, producing small pieces 450 with increased contact area with the body fluid. As a consequence, diffusion and resorption rates are increased while risk of clogging the flow of the body fluid and related complications decreased. The particles can be of any shape as long as the particles possess the desired magnetic property. As illustrative examples, the shape of the particles may be in an elongated form such as a rod or oblong, but spherical or other shapes may also be used. Certain shapes such as those with sharp edges may break the frame of the bulk implant material more easily than particles with more smooth edges. Suitable materials having the desired magnetic properties are well known in the art. Illustrative examples of magnetic materials that may be employed in this invention include metals, alloys, and metal oxides (such as iron, nickel, cobalt, gadolinium, other transition metals possessing ferromagnetic properties, and alloys or oxides thereof).

The resorption rate may be controlled by varying the size and amount (e.g., the volume percentage) of the aforementioned particles. The size of the particles or the size of the aggregates of particles is not critical so long as the particles are capable of causing fragmentation of the implant frame and afterwards being eliminated from the body by excretion, without triggering inflammation or blockage of fluid flow, or are capable of resorption by dissolution, degradation, disintegration or metabolic pathway. For illustration purposes, the size of the particles may be from about 5 nm to about 1 mm depending on the type of the implant. In some applications, the preferred size can vary from 5 nm to 1 $\mu$m. In other applications, the preferred size can vary from 1 $\mu$m to 100 $\mu$m, 100 $\mu$m to 500 $\mu$m, or 500 $\mu$m to 1 mm. There is no requirement that all the particles be of the same size.

The distribution of the particles in the bioresorbable bulk material need not be uniform, but uniformity may be preferred in certain circumstances. For example, concentration of embedded particles may be higher in the pigtail region of a ureteral stent to favor faster dissolution and quicker removal of the stent from the ureter. The volume percentage of the particles in the bioresorbable bulk material can be equal to or less than about 50% depending on factors including the particularities of the implant. In some embodiments, the volume percentage is less than 1% or greater, up to 50%.

The particles may be made of the same types of polymeric material as the bulk material but with a substantially different characteristics such that their resorption occur at a greater rate than the resorption of the bulk material such as lower molecular weight, lower crosslinking ratio (e.g., the number of crosslinks per crosslinkable sites or the number of crosslinks per unit volume or weight of the material), or different crosslinking ions (e.g. ions of a weaker electronic affinity). Characteristics of the polymeric material can be modulated by modifying factors such as these to suit the specific application at hand.

Controlling Resorption

In another aspect, the invention generally features methods for controlling resorption of a bioresorbable material for use in a medical device in a mammal. In one embodiment, a method for controlling resorption of a bioresorbable material in a medical device includes the steps of providing a bioresorbable bulk material, embedding resorbable particles in the bioresorbable bulk material, and contacting a body fluid with the bioresorbable bulk material having the embedded particles thereby causing the bioresorbable bulk material to resorb at a controllable resorption rate. The embedded particles have a different and faster resorption rate from that of the bulk material. The resorption rate of the bioresorbable bulk material is typically controlled to be faster with particles embedded in it than the resorption rate of the bioresorbable bulk material without the embedded particles.

Referring to FIG. 2 again and in one embodiment, the bioresorption is controlled by the swelling of the embedded particles 230 upon contact with a body fluid. Swelling may arise from, but is not limited to, chemical reactions or physical interactions upon the contact of the particles with a body fluid, such as the capture of some body fluid by the particle as in hydration, or release of gases. Continued swelling of the particles 240 weakens the matrix structure of the bioresorbable bulk material 220 and causes the medical implant frame to break up into small fragments 250, thereby preventing the large implant frame or fragments from clogging the flow of the body fluid. In addition, fragmentation into small pieces also results in an increased contact area of the bioresorbable bulk material 220 with the body fluid. The consequence is an increased fluid diffusion rate that promotes resorption and leads to the eventual mechanical degradation of the bioresorbable bulk material.

In one embodiment, particles having an agent that swells upon contact with the body fluid are incorporated into the bioresorbable bulk material during manufacture of a medical device. The agent and the particles swell within the matrix of the bioresorbable bulk material upon contact with the body fluid. In the case of ionically crosslinked polymeric materials, the swelling is especially effective in breaking up the implant frame after the ionic linkages of the crosslinked polymeric material have been partially removed by diffusion of crosslinking ions out of the matrix or by other means. The resorption rate of the implant can be modulated to fit a particular need. Typically, the presence of the particles favors a more homogeneous resorption of the implant material. Variance in the size of the fragments and in turn the resorption rate of the implant material may be achieved by varying the size, amount, shape, distribution, and/or nature of the particles within the implant. For example, a medical device may be manufactured with higher concentrations of highly swellable particles in the inner core of the device so as to have a slow onset of the resorption, followed by a rapid resorption of the inner core. Higher concentration may be used on an outer shell of the device to obtain an opposite result. For example, in the case of a ureteral stent, faster resorption of the kidney tail of the stent than the body of the stent may be desirable to favor the elimination or transportation of the stent out of the ureter into the bladder in a minimal amount of fragments. The partly resorbed stent would then continue to resorb at a slower rate into the bladder.

Referring to FIG. 3 again and in another embodiment, the bioresorption is controlled by the hydrolysis of the particles upon contact with a body fluid producing soluble by-products. Hydrolysis of the particles 330 into soluble by-products results in voids 340 in the matrix of the bioresorbable bulk material 320 and an increased porosity. As a consequence, the diffusion rate of the fluid into the implant 310 increases thereby promoting resorption and the eventual mechanical degradation of the material structure of the implant. The device as a result breaks into smaller fragments 350. In one embodiment, particles having an agent that hydrolyzes upon contact with the body fluid are incorporated into the bioresorbable bulk material during the manufacture of a medical implant device. The agent hydrolyzes within the matrix of the bioresorbable bulk material upon contact with the body fluid. Similar to the swelling agent, the resorption rate can be controlled by varying the size, shape, amount, and/or nature of the particles embedded in the bioresorbable bulk material. The resorption rate is also dependent on the hydrolizable agent and its amount used in the particles.

Referring to FIG. 4 again and in another embodiment, the bioresorption is controlled by activation and/or vibration of the embedded particles responding to a magnetic field. The methods for controlling resorption of a bioresorbable material include providing a bulk material 420 that is bioresorbable and is embedded with particles 430 having magnetic, paramagnetic, and/or superparamagnetic properties, creating a magnetic field surrounding the particles, and inducing activation or vibration of the particles by modulating the magnetic field 440 thereby causing resorption of the bulk material at a controllable rate. The implant breaks into smaller fragments 450. These particles may include a magnetic material, a paramagnetic material, and/or a superparamagnetic material.

In one detailed embodiment, inducing activation and/or vibration of the particles is by time-varying the magnetic field surrounding the particles. The magnetic field establishes forces that compel the magnetic, paramagnetic, or superparamagnetic particles to move within the matrix of the material lodging the particles. The moving and/or vibrating of the embedded particles within the matrix of the bioresorbable bulk material causes fragmentation of the implant frame, producing small pieces with increased contact area with a body fluid. As a consequence, diffusion and resorption rates are increased while risk of clogging the fluid flow and related complications decreased. The magnetic field surrounding the particles may be supplied by a magnetic field generator within the body of the subject being treated. The magnetic field can also be supplied by a magnetic field generator outside of the subject's body. The field strength of the magnetic field that may be employed depends on the size and nature of the particles and the desired rate of resorption. In one embodiment, the magnetic field at the site is oscillating in strength as a function of time and/or coordination. The resorption rate can also be controlled by varying the size, shape, and/or amount of the particles embedded in the bioresorbable bulk material. Furthermore, the resorption rate is dependent on the nature and amount of the magnetic material used in the particles and the orientation of the particles relative to the magnetic field.

Similarly, particles that respond to microwave, ultrasound, or radio frequencies may be embedded in the implant bulk material. Movement or vibration of these particles responding to microwave, ultrasound, or radio frequencies causes fragmentation of the implant frame.

Figure 5:
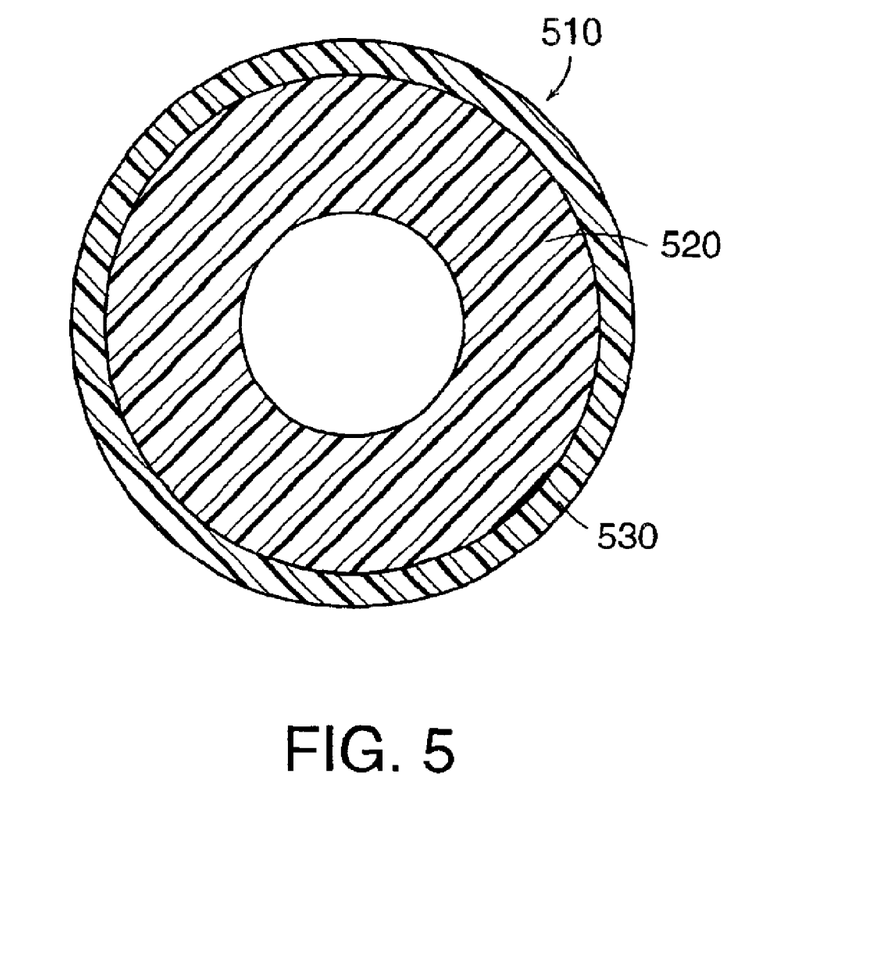
FIG. 5 is a cross-sectional schematic view of an embodiment of a medical device according to the invention, illustrating the control of resorption by providing a coating on the implant material.

In another embodiment, as illustrated in FIG. 5, resorption of a bioresorbable material is controlled by a coating on a medical device. The methods for controlling resorption of a bioresorbable material include providing a bulk material 520 that is bioresorbable and shaped as a medical device, here a stent 510, and coating the medical device with a coating material 530. The coating material 530 includes a dissolvable polymeric material and allows diffusion of a body fluid through the coating material at a pre-selected rate. Coating of the medical device may be by any conventional coating methods including solvent and hot-melt processes. The medical device can be completely or only partially coated. The diffusion rate can be controlled by varying the size, thickness, and/or the nature of the coating material on the device. For example, a coating that is more hydrophobic tends to slow down the diffusion rate into the implant.

In yet another aspect, the invention features a coating material for use in a medical device for regulating resorption of the medical device. The coating serves as a controlled barrier to diffusion. The coating material includes a bioresorbable ionically or covalently crosslinked polymeric material that allows diffusion into the medical device by a body fluid at a pre-selected rate. The device can be completely or only partially coated. Illustrative examples of such coating material include a hydrogel, such as hyaluronic acid and polyslip, and thermoplastic material, such as polyurethane and polyethylene. The coating material may be applied to a device by melt, solvent, spray or other processes known to the artisan. The coating material can also include a lubricity-controlling agent.

Figure 6:
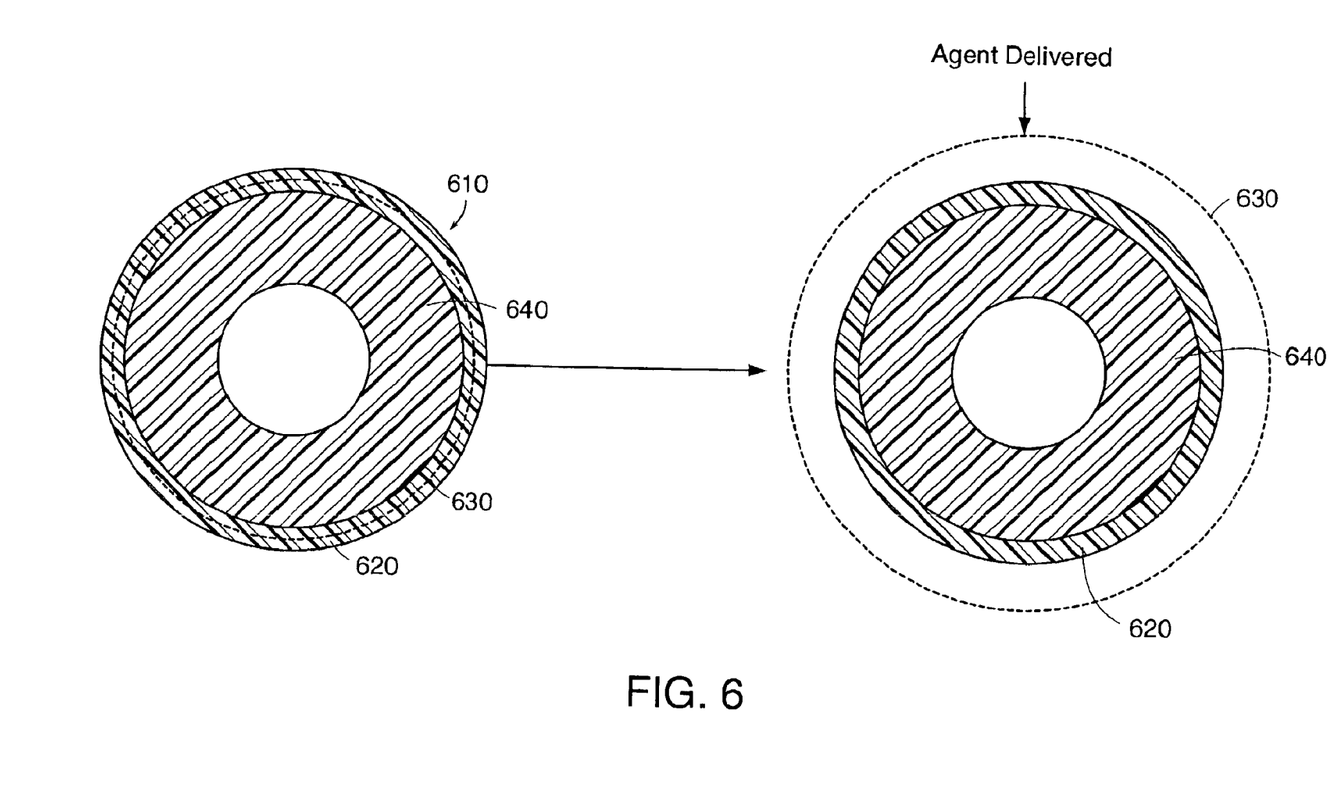
FIG. 6 is a cross-sectional schematic view of an embodiment of a medical device according to the invention, illustrating the control of delivery of an embedded pharmaceutical agent.

Referring to FIG. 6, a system can be constructed for a controlled delivery of a pre-selected pharmaceutical agent to a location within the body of a mammal. This system includes a carrier device 610 with a coating that has a bioresorbable ionically or covalently crosslinked polymeric material. The pharmaceutical agent to be delivered can be incorporated into the coating material 620 as macro-particles embedded therein. The pharmaceutical agent can also be incorporated into the coating material in bulk at the molecular level. The pharmaceutical agent 630 diffuses out of the coating material 620 upon contacting a body fluid by the coating material 620. The inner core 640 may be constructed to provide necessary mechanical support for the coating layer. The inner core 640 may or may not be needed depending on the application. The carrier can be any device that is capable of carrying the pre-selected pharmaceutical agent such as antimicrobial or antibiotic agents. The agent loading can generally be from about 0.01% to about 40% depending on the agent and the need of the treatment.

Compositions of the present invention may be produced by any conventional ways of forming a mixture with two or more components. The compositions may be prepared by mixing precursor components followed by a chemical processing of either the particles or the bulk material. For example, a conventional mechanical mixer may be sufficient to produce a composition having particles of desired properties and a bioresorbable material. A solvent may be used so that a solution of the bulk bioresorbable material is mixed with the particles followed by removal of the solvent. Such methods include first mixing precursor(s) of the bioresorbable bulk material with the particles followed by a reaction of the precursor(s) to produce the bioresorbable bulk material. Also, one can first mix precursor(s) of the particles with the bioresorbable bulk material followed by a reaction of the precursor(s) to produce the desired particles. Chemical modifications that may be used in preparing the compositions of the invention include, but are not limited to, polymerization, crosslinking reactions either ionic or covalent so as to gel, cure, or set a precursor polymer.

The devices (or components of devices) of the present invention may be made via various manufacturing processes including injection molding, extrusion, rotational molding, compression, roll wrapping, etc. For example, one way to produce a stent is to first mix particles of the desired properties with an extrudable and bioresorbable material and then extrude the mixture to form a stent using conventional extrusion techniques. Another method is to wrap a sheet or film of the mixture around a cone-shaped mandrel. Yet another method is to employ a pultrusion process where the mixture of the bioresorbable material and particles are pulled from a pultrusion die having the desired cross-sectional profile.

The devices of the present invention may be used for any treatment involving a medical implant that needs a controlled resorption rate. For example, a ureteral stent made with the compositions of the present invention may be placed in a patient. The stent will then resorb at a rate dependent on the composition of the material. The stent can be set to resorb quickly or slowly by pre-selecting its composition as described earlier. Devices can also be constructed to effect drug delivery as described above.

EXAMPLE 1

A syringe pump is connected to three syringes. Syringe One contains an alginate solution. Syringe Two contains a calcium carbonate solution. Syringe Three contains the same alginate solution as in Syringe One plus resorbable fine particles of an alginate at a different molecular weight than that in Syringe One. The contents of the three syringes are injected into a tube connected to the three syringes and then pushed into a static mixer made of silicone tubing. After mixing, the content of the static mixer then travels to a tubular shaped cavity and a rod so positioned that a tubular shaped device is molded and gels. Alternatively, a port having the desired features can be used to form a desired medical device. Normally, extrusion is first done into a low pH buffer solution wherein calcium ions partially diffuse out. A second crosslinking is then carried out producing the final device.

EXAMPLE 2

Example 1 is repeated except resorbable fine particles having polylactic acid are used.

EXAMPLE 3

A segment of the tubing produced in Example 1 is soaked in a simulated body fluid such as urine for 48 hours. Samples from the soaked tubing are placed under microscope and compared with samples from a unsoaked tubing. It is expected that the soaked samples will have broken down into fragments or display cracking in the frame of the implant.

EXAMPLE 4

A segment of the tubing produced in Example 2 is soaked in a simulated body fluid such as urine for 48 hours. Samples from the soaked tubing are placed under microscope and compared with samples from the unsoaked tubing. It is expected that the soaked samples will exhibit significantly hydrolyzed particles and voids so created.

Variations, modifications, and other implementations of what is described herein will occur to those of ordinary skill in the art without departing from the spirit and the scope of the invention. Accordingly, the invention is not to be limited by the preceding illustrative description.

What is claimed is:

1. A medical device for use in a mammal comprising:
   (a) a bioresorbable bulk material comprising an ionically or covalently crosslinked polymeric material; and
   (b) resorbable particles containing an agent that causes swelling of the particles upon contact with a body fluid, said particles embedded in said bioresorbable bulk material and said swelling of the particles causing fragmentation of said bioresorbable bulk material.

2. The medical device of claim 1 wherein said resorbable particles resorb upon contact with a body fluid at a resorption rate that is different from the resorption rate of said bioresorbable bulk material.

3. The medical device of claim 2 wherein the resorption rate of said resorbable particles is greater than the resorption rate of said bioresorbable bulk material.

4. The medical device of claim 1 wherein said bioresorbable bulk material comprises an ionically crosslinked polymeric material.

5. The medical device of claim 1 wherein said bioresorbable bulk material comprises a covalently crosslinked polymeric material.

6. The medical device of claim 4 wherein said ionically crosslinked polymeric material comprises at least one polymer or copolymer made from at least one member of the group consisting of polyacrylic acids, polymethacrylic acid, polyethylene amine, polysaccharides, alginic acid, pectinic acids, carboxy methyl cellulose, hyaluronic acid, heparin, chitosan, carboxymethyl chitosan, carboxymethyl starch, carboxymethyl dextran, heparin sulfate, chondroitin sulfate, cationic starch, and salts thereof.

7. The medical device of claim 4 wherein said ionically crosslinked polymeric material is an ionically crosslinked polymer hydrogel and has a water content of less than 90% by weight and possesses sufficient mechanical strength to serve as a stent, a catheter, a cannula, a plug, a constrictor, a sheet, a filler, a bone anchor, a plate, a rod, a seed, a tube, or a portion thereof.

8. The medical device of claim 1 wherein said medical device is a stent, a catheter, a cannula, a plug, a constrictor, a sheet, a filler, a bone anchor, a plate, a rod, a seed, a tube, or a portion thereof.

9. The medical device of claim 1 wherein each of said resorbable particles comprises an organic compound.

10. The medical device of claim 1 wherein each of said resorbable particles comprises a soluble or degradable inorganic compound.

11. The medical device of claim 9 wherein said organic compound is a sugar or a water soluble organic salt.

12. The medical device of claim 1 wherein each of said resorbable particles comprises an organic or inorganic crystal or powder aggregate.

13. The medical device of claim 1 wherein each of said resorbable particles comprises a water-swellable polymer.

14. The medical device of claim 13 wherein said water-swellable polymer comprises a material selected from the group consisting of polysaccharides, polyglycolic acid, polylactic acid, cellulose derivatives, hyaluronic acid, and colloid/hydrogel.

15. The medical device of claim 1 wherein the size of each of said resorbable particles is from about 5 nm to about 1 mm.

16. The medical device of claim 1 wherein the ratio of said resorbable particles in said bioresorbable bulk material is equal to or less than about 50% by volume.

17. The medical device of claim 1 wherein each of said resorbable particles comprises a polymer selected from the group consisting of polysaccharides, polyglycolic acid, polylactic acid, and polycaprolactone and copolymers of any two or three of glycolic acid, lactic acid, and caprolactone monomers.

18. A method for controlling resorption of a bioresorbable material in a device for use in a mammal, said method comprising:
(a) providing a bioresorbable bulk material comprising an ionically or covalently crosslinked polymeric material;
(b) embedding resorbable particles in said bioresorbable bulk material, said resorbable particles resorbing faster upon contact with a body fluid than said bioresorbable bulk material; and
(c) contacting a body fluid with said bioresorbable bulk material and said resorbable particles, wherein the resorbable particles swell upon contact with said body fluid and cause fragmentation of said bioresorbable bulk material.

19. The method of claim 18 wherein said controllable resorption rate is different from the resorption rate of said bioresorbable bulk material without said embedded resorbable particles.

20. The method of claim 19 wherein said bioresorbable bulk material comprises an ionically crosslinked polymeric material.

21. The method of claim 19 wherein said bioresorbable bulk material comprises a covalently crosslinked polymeric material.

22. The method of claim 19 wherein said resorption rate is controlled by varying the size or the amount of said resorbable particles.

23. The method of claim 19 wherein said resorbable particles hydrolyze into by-products soluble in said body fluid upon contact with said body fluid.

24. A composition for use in a device in a mammal, said composition comprising:
(a) a bioresorbable bulk material comprising an ionically or covalently crosslinked polymeric material; and
(b) resorbable particles containing an agent that causes swelling of the particles upon contact with a body fluid, said particles embedded in said bioresorbable bulk material, and said swelling of the resorbable particles causing fragmentation of said bioresorbable bulk material.

25. The composition of claim 24 wherein the resorption rate of said resorbable particles is greater than the resorption rate of said bioresorbable bulk material.

26. The composition of claim 24 wherein said bioresorbable bulk material comprises an ionically crosslinked polymeric material or a covalently crosslinked polymeric material.

27. The composition of claim 24 wherein each of said resorbable particles comprise an organic compound.

28. The composition of claim 24 wherein each of said resorbable particles comprise a soluble or degradable inorganic compound.

29. The composition of claim 24 wherein each of said resorbable particles comprise organic or inorganic crystals or powder aggregates.

30. The composition of claim 24 wherein each of said resorbable particles comprise a polymer.

31. The composition of claim 24 wherein the size of said resorbable particles is about 5 nm to about 1 mm.

32. The composition of claim 24 wherein the volume percentage of said resorbable particles in said bulk material is equal to or less than about 50%.

33. The medical device of claim 1 wherein said resorbable particles comprise an ionically or covalently crosslinked polymeric material that is the same kind of ionically or covalently crosslinked polymeric material as said bioresorbable bulk material.

34. The medical device of claim 33 wherein said polymeric material of said resorbable particles is crosslinked at a lower ratio than the crosslinking ratio of said polymeric material of said bioresorbable bulk material.

35. The medical device of claim 33 wherein said polymeric material of said resorbable particles and bulk material are crosslinked with ions said ions of said resorbable particles having a weaker electronic affinity than said ions of said bioresorbable material.

* * * * *

UNITED STATES PATENT AND TRADEMARK OFFICE
CERTIFICATE OF CORRECTION

PATENT NO. : 6,913,765 B2
APPLICATION NO. : 09/813780
DATED : July 5, 2005
INVENTOR(S) : Jianmin Li et al.

It is certified that error appears in the above-identified patent and that said Letters Patent is hereby corrected as shown below:

Column 1,
Line 36, after "implants", delete ".", and insert -- , --.
Line 41, change "endoscope" to -- endoscopic --.

Column 2,
Line 4, delete "and".
Line 5, change "possesses" to -- possessing --.

Column 6,
Line 19, change "entire", to -- entirety --.
Line 26, after "as", insert -- an --.

Column 8,
Line 1, after "while" insert -- the --.
Line 2, after "complications" insert -- are --.
Line 8, delete "more".
Line 9, change "smooth" to -- smoother --.
Line 61, after "particles", insert -- , --.

Column 10,
Line 56, change "methods", to -- method, --.

Column 12,
Lines 29 and 39, after "fluid", insert -- , --.
Lines 29 and 39, after "urine", insert -- , --.

UNITED STATES PATENT AND TRADEMARK OFFICE
CERTIFICATE OF CORRECTION

PATENT NO. : 6,913,765 B2
APPLICATION NO. : 09/813780
DATED : July 5, 2005
INVENTOR(S) : Jianmin Li et al.

It is certified that error appears in the above-identified patent and that said Letters Patent is hereby corrected as shown below:

<u>Column 14,</u>
Line 62, after "and", insert -- said bioresorbable --.
Line 63, after "ions", insert -- , -- (first occurrence).

Signed and Sealed this

Twenty-seventh Day of June, 2006

JON W. DUDAS
*Director of the United States Patent and Trademark Office*